Figure 1:
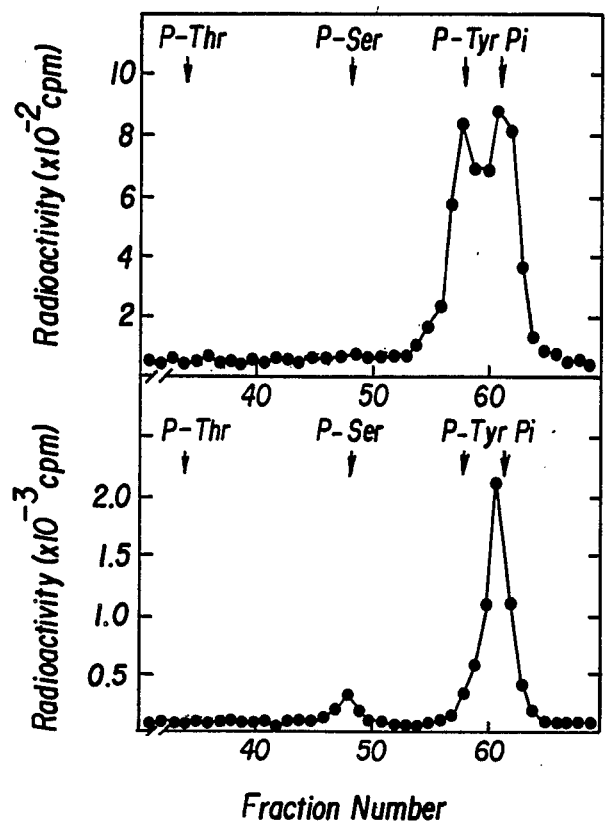

United States Patent [19]

Liang et al.

[11] Patent Number: 4,710,469
[45] Date of Patent: Dec. 1, 1987

[54] NOVEL PHOSPHOTYROSYL PROTEIN PHOSPHATASE

[75] Inventors: Theming Liang, Miami, Fla.; Eve E. Slater, Short Hills, N.J.

[73] Assignee: Merck & Co., Inc., Rahway, N.J.

[21] Appl. No.: 858,622

[22] Filed: May 2, 1986

[51] Int. Cl.$^4$ ............................................. C12N 9/12
[52] U.S. Cl. ...................................... 435/194; 530/352
[58] Field of Search ......................... 435/194; 530/352

[56] References Cited

PUBLICATIONS

Shriver et al., J. Bio. Chem., 259, pp. 11383–11399 (1984).
Swarup et al., J. Biol. Chem., 256, pp. 8187–8201 (1981).
Li et al., Eur. J. Biochem., 138, pp. 45–51 (1984).
Foulkes et al., J. Biol Chem., 258, pp. 431–438 (1983).
Chernoff et al., Arch. Biochem. Biophys., 226, pp. 517–550 (1983).
Brautigan et al., J. Biol. Chem., 256, pp. 6519–6522 (1981).

Primary Examiner—Howard E. Schain
Attorney, Agent, or Firm—David L. Rose; Michael C. Sudol, Jr.

[57] ABSTRACT

A glycoprotein phosphotyrosyl protein phosphatase is isolated from human tissues, such as human placental membrane. Upon membrane solubilization and extraction of the enzyme it was subjected to chromatographic purification and isolation. The analytical and biological responses of the enzyme demonstrate that it is novel and readily distinguished from other enzymes previously isolated from similar tissues. The enzyme is a dephosphorylation enzyme of membrane phosphoprotein kinases, and as such has utility as an antidiabetic agent, an antiatherosclerosis agent or an antitumor agent since certain membrane receptor kinases involved in each such biological function involve a phosphorylation mechanism for cell transformation, metabolism and growth and which, when blocked by the instant enzyme, results in a suppression or alteration of the biological function.

4 Claims, 9 Drawing Figures

Fractionation of Lectin Eluate
by Preparative DEAE-HPLC

NOVEL PHOSPHOTYROSYL PROTEIN PHOSPHATASE

BACKGROUND OF THE INVENTION

Human placental membrane alkaline phosphatases and human prostatic cytosol acid phosphatases have been isolated and purified. However, such enzymes differ from the instant enzyme in the analytical properties of each and also in biological properties since the previously isolated enzymes have vastly different inhibition sensitivities when compared with the instant enzyme.

SUMMARY OF THE INVENTION

The instant invention relates to a novel enzyme isolated from human membranes with a large number of insulin receptors and to the isolation and purification of such enzyme. Thus, it is an object to define the novel enzyme in terms of its analytical and biological properties. It is a further object to define the novel techniques used to isolate and purify the enzyme from the tissue with which it originates. A still further object is to define the utility of such an enzyme. Further objects will become apparent from a reading of the following description.

DESCRIPTION OF THE INVENTION

Certain enzymes present in various tissues control biological processes by promoting or inhibiting biochemical events of metabolism, growth and transformation. Examples of such agents are tyrosine protein kinases which are necessary for cell growth. Receptors for insulin, epidermal growth factor, platelet derived growth factor and insulin-like growth factor have tyrosine protein kinases capable of both autophosphorylation and transphosphorylation. Also certain retroviral oncogene products are tyrosine protein kinases. Thus, phosphatases, and in particular phosphotyrosyl protein phosphatases, are likely to play an important role in the control of hormone action and viral transformation.

Several reports have described phosphotyrosyl protein phosphatases which are distinct from phosphoserine or phosphothreonine protein phosphatase. See Foulkes et al., *J. Biol. Chem.* 258, pp. 431-438 (1983) and Chernoff et al., *Arch. Biochem. Biophys.* 226 pp. 517-550 (1983). The differences in their inhibitor sensitivities indicate that at least several different classes of phosphotyrosyl protein phosphatases exist, with only a few of these enzymes having been purified. One class of phosphotyrosyl phosphatases is inhibited by zinc ions; two such enzymes have been purified from rabbit kidney cytosol. Alkaline phosphatase purified from several membrane sources, including placenta, and acid phosphatase purified from human prostatic cytosol have also been shown to prefer phosphotyrosyl proteins over phosphoserine proteins as substrate. See Brautigan et al., *J. Biol. Chem.* 256 pp. 6519-6522 (1981); Shriver et al., *J. Biol. Chem.* 259 pp. 11383-11399 (1984); Swarup et al., *J. Biol. Chem.* 256 pp. 8187-8201 (1981); and Li et al., *Eur. J. Biochem.* 138 pp. 45-51 (1984). The instant invention is concerned with a new enzyme, distinct from the previously described phosphatases, which is isolated from human tissues high in insulin receptors.

In diabetes, in the formation of atherosclerotic plaques and in tumor formation certain receptor sites involve a phosphate group or tyrosine protein kinase which through phosphorylation activates the enzyme or binds the enzyme to appropriate receptor sites. Certain of these processes are natural processes such as insulin binding, and certain processes are unnatural processes such as unwanted vascular growth in diabetics, atherosclerotic plaque formation or tumor formation. The enzyme of the instant invention is capable of dephosphorylation of tyrosine protein kinases which can lead to the blocking of detrimental vascular growth as is seen in diabetic retinopathy; in the blocking of the formation of atherosclerotic plaque formation thus avoiding the complications of atherosclerosis suchas myocardial infarction, thrombosis formation, and stroke; and a mechanism for blocking the formation of certain tumors, such as those which require retroviral oncogene products for example pp 60 src. In other processes, the dephosphorylation enzyme of this invention can block insulin receptor action thus preventing some or many aspects of insulin action, a natural process, which can provide for a screening mechanism for drugs effective at improving insulin resistance.

The phosphotyrosyl protein phosphatase enzyme of this invention is isolated from those human tissues which are relatively high in insulin receptors. Examples of such tissues are placental membrane, liver, adipose, brain muscle, and the like. The extraction of the enzyme is carried out in the steps of (1) removing unnecessary supporting membranes from the tissue, (2) homogenizing the remaining tissue, (3) centrifuging the homogenate in an aqueous buffer to remove solid tissue debris, (4) ultracentrifuging the supernatant to concentrate the enzyme containing membrane material, (5) solubilizing the washed membrane material and removing the unsolubilized residue and (6) extraction and purification of the enzyme from the solubilized membrane protein with chromatographic techniques.

In the instant application certain abbreviations are employed which may be generally recognized by those skilled in the art but are fully defined here in order to ensure the avoidance of all ambiguity.

| Abbreviation | Meaning |
| --- | --- |
| ATP | Adenosine triphosphate |
| BSA | Bovine serum albumin, crystallized and lyophilized |
| cAMP | Cyclic adenosine monophosphate |
| DEAE | Diethylaminoethyl |
| DTT | Dithiothreitol |
| EDTA | Ethylene diamine tetraacetate |
| EGF | Epidermal growth factor |
| HEPES | n-2-Hydroxyethylpiperazine-N'—2-ethane sulfonic acid |
| IGT | Buffer-imidazole (40 mM), glycerol (10%) and triton X-100 (0.2%) |
| Mr | Molecular weight |
| PMSF | Phenylmethylsulfonylfluoride |
| PNPPase | p-Nitrophenylphosphate phosphatase |
| PNPP | p-Nitrophenylphosphate |
| Pi | Inorganic phosphate |
| SDS | Sodium dodecyl sulfate |
| Ser | Serine |
| TCA | Trichloroacetic acid |
| TFA | Trifluoroacetic acid |
| Thr | Threonine |
| Tris | Hydroxymethylaminomethane |
| Tyr | Tyrosine |

The tissues which are to provide the source of the new enzyme are initially treated to remove supporting membranes and connective tissues which do not contain the enzyme. The remaining tissue is homogenized in order to physically break down the cell to release the cell material, including the enzyme. The homogenization is carried out using standard techniques and usually in the presence of an aqueous buffer solution. Using fractional centrifugation the heavier tissue debris is removed leaving the enzyme-containing tissue material suspended in the buffer solution. Further ultracentrifugation produces a precipitate, commonly referred to as a "pellet" of enzyme-containing tissue material.

To release the enzyme from the homogenized cell material, the centrifugal pellet of tissue material is treated with a detergent and emulsifying agent such as octoxynol, sold under the trade name of "Triton X-100". The detergent, usually provided as an aqueous solution, solubilizes the tissue material and releases the enzyme from such tissue material. After removal of any unsolubilized tissue by ultracentrifugation, the solubilized tissue and enzyme is purified using normal purification techniques known to those skilled in the art such as chromatographic techniques, for example column, thin layer, preparative layer and high pressure liquid chromatography.

The human phosphotyrosyl protein phosphatase enzyme of this invention has not yet been precisely characterized as to its structure. However, during its isolation, purification and subsequent analytical and biological studies, sufficient characterizing information has been obtained which clearly demonstrates that the enzyme is pure and significantly different from other enzymes isolated from similar tissues.

The enzyme has a molecular weight of approximately 200,000 as shown by gel filtration on a TSK HPLC column in the presence of 0.2% octoxynol and a subunit molecular weight of approximately 73,000 as shown by SDS reducing gel electrophoresis.

Other analytical data which characterize the instant enzyme are responses to a variety of protein phosphatase inhibitors, pH-activity profile, unique immunologic profile and subunit specificity.

The instant phosphotyrosyl protein phosphatase is also characterized by its biological activities. The enzyme has been observed to be a dephosphorylating agent and the effects on this dephosphorylation by various phosphatase inhibitors can be readily employed to characterize the enzyme and also differentiate it from other enzymes. Table I below shows the effect of phosphatase inhibitors on the instant enzyme and also on a placental alkaline phosphatase and a prostatic acid phosphatase. The percentage change of the effects of the enzyme in response to the specified amounts of phosphatase inhibitors are reproducible characteristics of the enzyme and can differentiate it from other enzymes. The other enzymes are shown for comparison purposes and to show the significant differences between the instant enzyme and the others.

TABLE I

Effects of Various Compounds on Activities of Human Placental Alkaline Phosphatase, Prostatic Acid Phosphatase, and Purified Phosphotyrosyl Protein Phosphatase

|  | Placental Alkaline Phosphatase | | Prostatic Acid Phosphatase | | Purified Phosphotyrosyl Protein Phosphatase | |
| --- | --- | --- | --- | --- | --- | --- |
|  | mU | % | mU | % | mU | % |
| control | 0.437 |  | 1.491 |  | 0.994 |  |
| 10 μM molybdate | 0.437 | 0 | 0.074 | −95.0 | 0.0361 | −96.4 |
| 5 mM L-tartrate | 0.391 | −10.4 | 0.036 | −97.6 | 0.019 | −98.1 |
| 5 mM NaF | 0.433 | −1.0 | 0.0 | −100 | 0.0323 | −96.7 |
| 20 mM EDTA | 0.027 | −94.0 | 1.467 | −2.2 | 1.778 | +78.9 |
| 100 μM ZnCl$_2$ | 0.853 | +95.2 | 1.372 | −8.0 | 0.845 | −14.9 |
| 10 μM vanadate | 0.357 | −18.3 | 0.181 | −87.8 | 0.614 | −38.2* |
| 10 mM p-tyrosine | 0.063 | −85.6 | 1.127 | −24.4 | 0.779 | −21.6 |
| 10 mM p-serine | 0.032 | −92.6 | 1.208 | −19.0 | 1.723 | +73.4 |

Human placental alkaline phosphatase and prostatic phosphatase were obtained commercially. Alkaline phosphatase was assayed in a reaction mixture containing 50 mM glycine NaOH, pH 10, MgCl$_2$ and 1 mM PNPP; prostatic acid phosphatase was assayed in a reaction mixture containing 100 mM acetate, pH 5, 0.1 mM PNPP, and purified phosphotyrosyl protein phosphatase was assayed in 100 mM acetate, pH 5, 0.8 mM PNPP, 0.2 mg/ml BSA and 5 mM DTT. All assays were performed at 30°.

The instant enzyme is still further characterized by the various analytical and biological procedures which are employed in its isolation and purification. In conjunction with these procedures, FIGS. 1 to 9 are appended hereto and are described as follows:

FIG. 1. Phosphoamino Acid Analysis of Partially Hydrolyzed $^{32}$P-Ser-casein and $^{32}$P-Tyr-casein. Samples of $^{32}$P-Ser-casein and $^{32}$P-Tyr-casein were hydrolyzed with 6N HCl under vacuum at 100° C. for 2 hours. Samples containing approximately 12,000 cpm of radioactivity were loaded on a Synchropak Q300 column equilibrated with 40 mM potassium phosphate, pH 4. The column was eluted isocratically with the same buffer at a flow rate of 1.5 ml/minute and 0.2 minute fractions were collected and counted in 10 ml Aquasol II. Phosphothreonine, phosphoserine and phosphotyrosine standards were detected by monitoring absorbance at 214 nm wavelength. A, $^{32}$P-Ser-casein. B, $^{32}$P-Tyr-casein.

Figure 2:
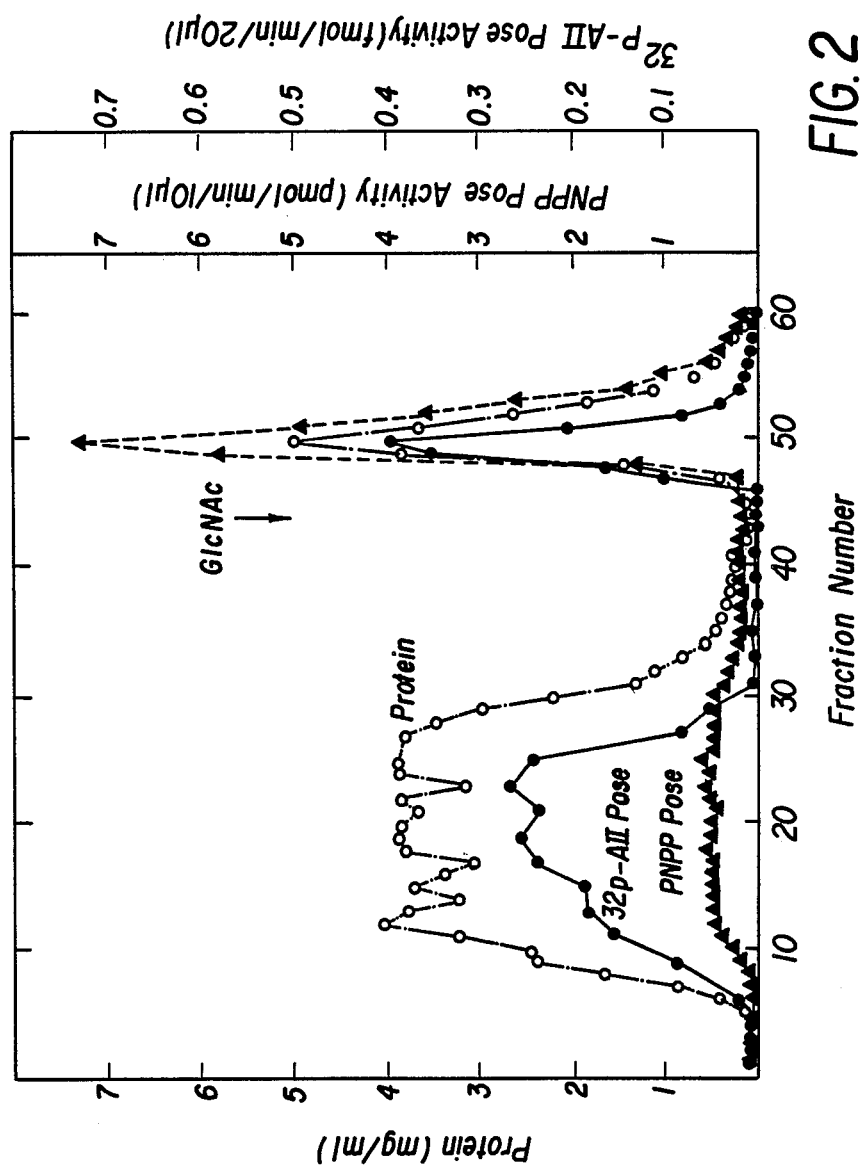

FIG. 2. Fractionation of Solubilized Human Placental Membranes by Wheat Germ Lectin Agarose Affinity Chromatography. Solubilized human placental membrane protein (400 mg) was loaded onto 40 ml of wheat germ lectin agarose equilibrated with a buffer containing 40 mM imidazole, pH 7.2, 10% glycerol, 0.2% Triton X-100, and 0.5M NaCl. After washing the column with the same buffer, elution was done with 0.3M N-acetyl glucosamine in the same buffer. 5 ml fractions were collected. Aliquots were taken for the determination of protein, and phosphatase activity against PNPP (1 mM at pH 5) and $^{32}$P-Tyrangiotensin II (pH 5).

Figure 3:
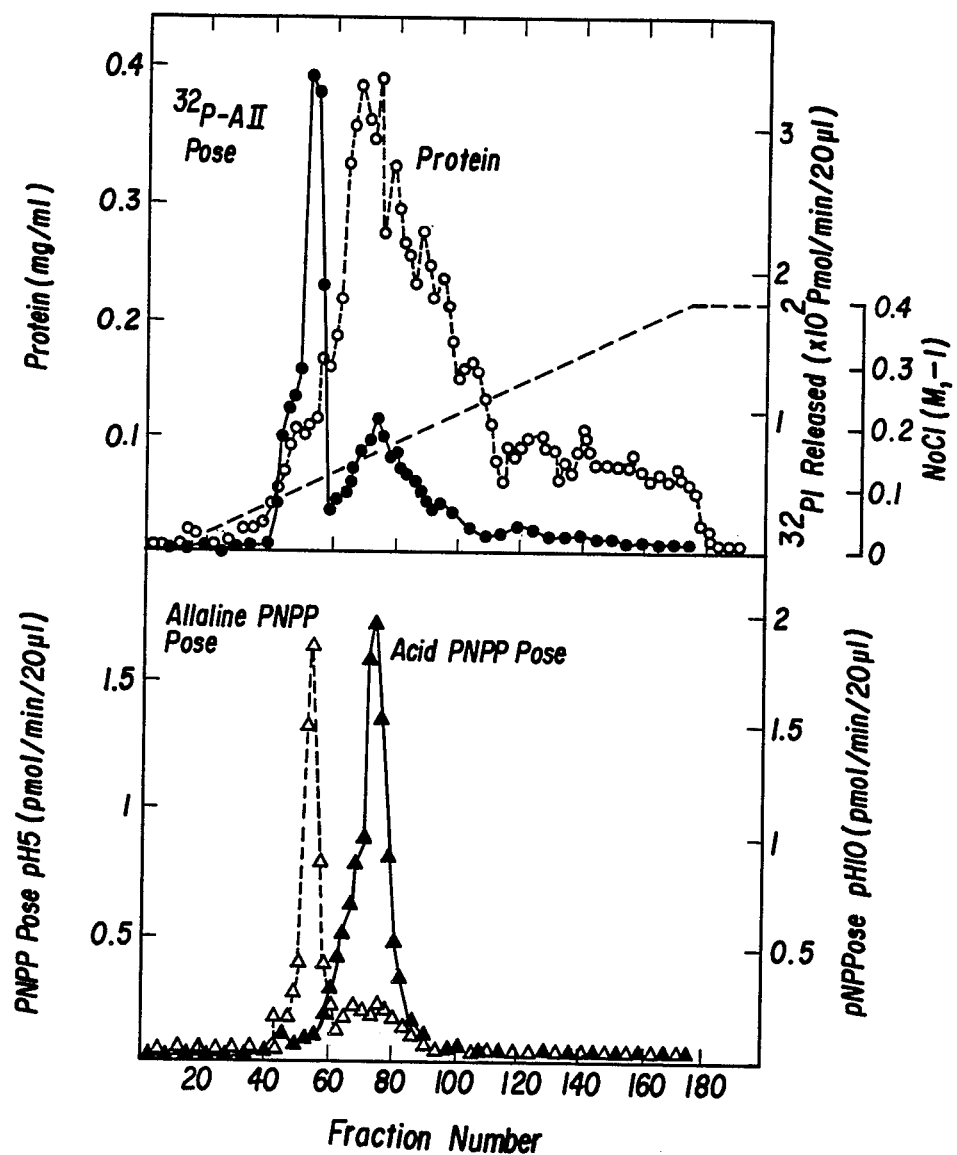

FIG. 3. Fractionation of the Lectin Eluate by Preparative DEAE-HPLC. Fractions eluted by N-acetylglucosamine from the lectin column were pooled and dialyzed against IGT buffer and loaded onto a preparative DEAE-HPLC column. The column was eluted with a linear NaCl gradient (0-0.4M) collecting 5 ml fractions. This chromatography resolved two peaks of $^{32}$P-angiotensin II phosphatase activities. One of these corresponded to the peak of alkaline PNPPase activity eluted at 0.1M NaCl. Further purification was done by pooling the three fractions containing the 32P-angiotensin II phosphatase peak of activity eluted at 0.15M NaCl. This peak corresponded to a peak of acidic PNPPase activity.

Figure 4:
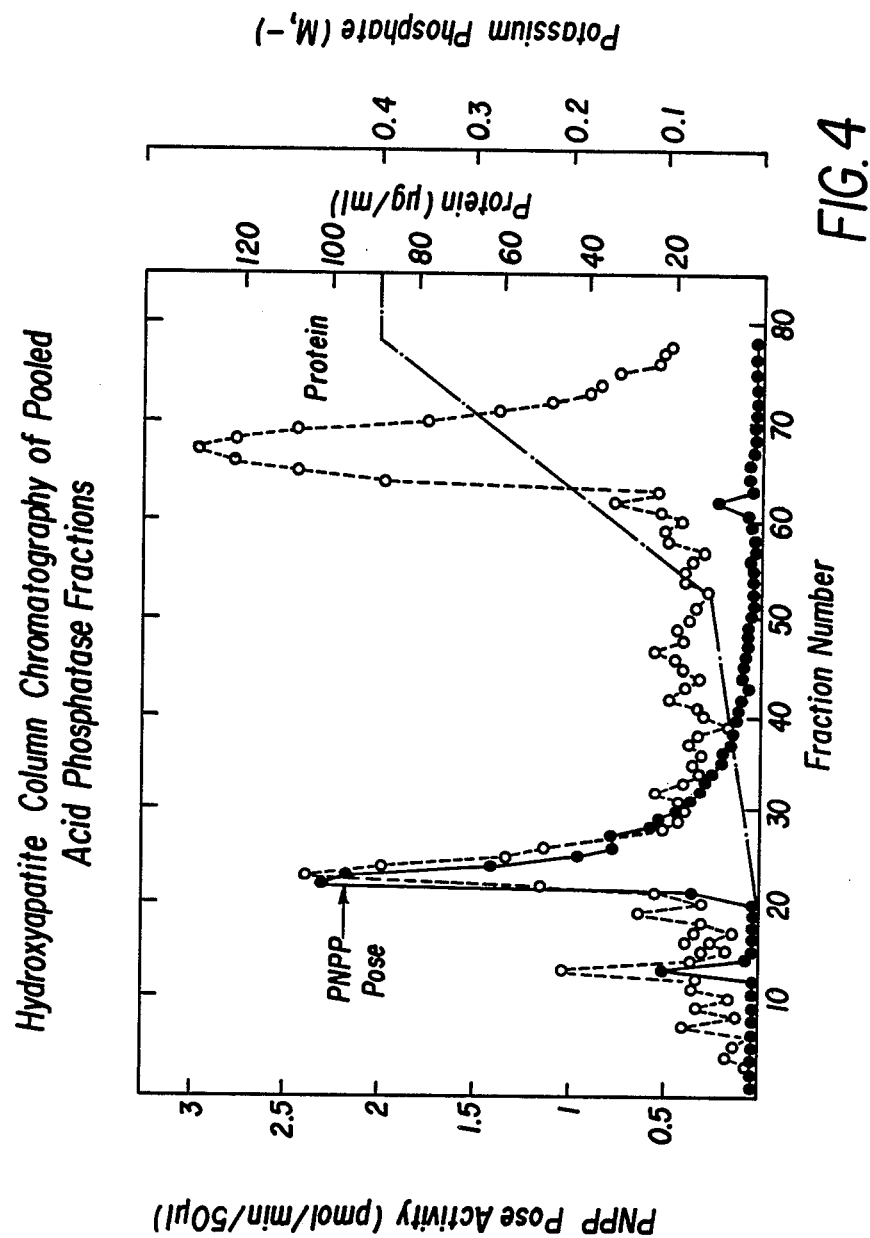

FIG. 4. Hydroxyapatite Column Chromatography pooled fractions from the preparative DEAE HPLC column were loaded onto 20 ml of hydroxyapatite equilibrated with IGT buffer and eluted initially with a 0–50 mM phosphate followed by a 50–400 mM phosphate gradient. A minor peak of acidic PNPPase activity was unretained while the major PNPPase activity was eluted at around 5 mM phosphate. The $^{32}$P-Tyr angiotensin II phosphatase activity showed a similar profile.

Figure 5:
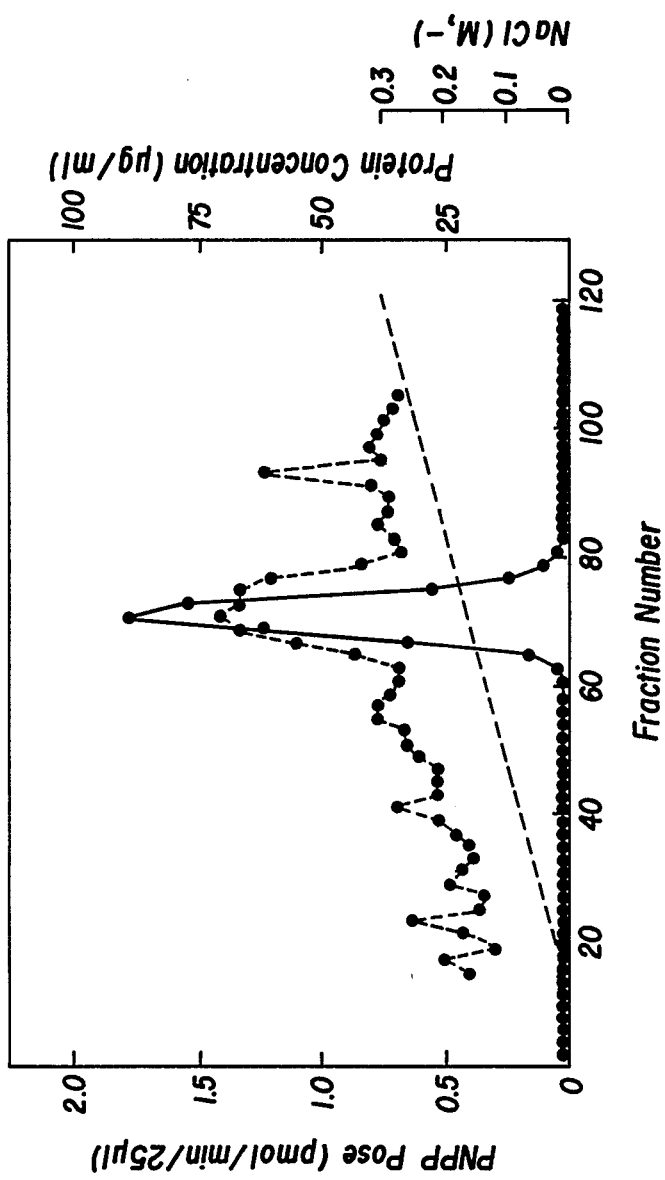

FIG. 5. Second DEAE HPLC Column Pooled fractions from the hydroxyapatite column were dialyzed and rechromatographed on a second DEAE HPLC column. Similar conditions were employed as in FIG. 3 except that a 0–0.3M NaCl gradient was used.

Figure 6:
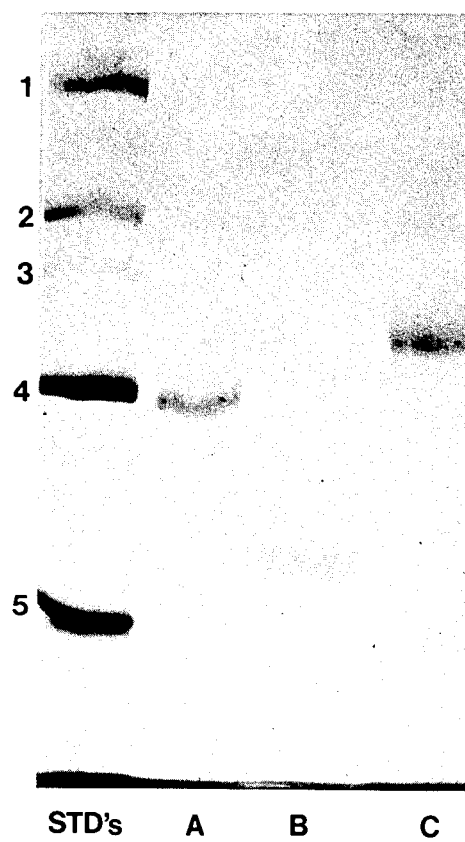

FIG. 6. SDS Gel Electrophoresis of the Purified Enzyme Preparation. 2–5 μg protein of (A) commercially available human placental alkaline phosphatase were subjected to gel electrophoresis on a 7.5% polyacrylamide gel. Proteins were stained with silver nitrate. Standards were: (1) myosin, Mr 200,000, (2) B galactosidase, Mr 116,250, (3) phosphorylase B, Mr 92,500, (4) bovine serum albumin, Mr 66,200, and (5) ovalbumin, Mr 45,000, (B) human prostatic acid phosphatase, and (C) the purified enzyme preparation.

Figure 7:
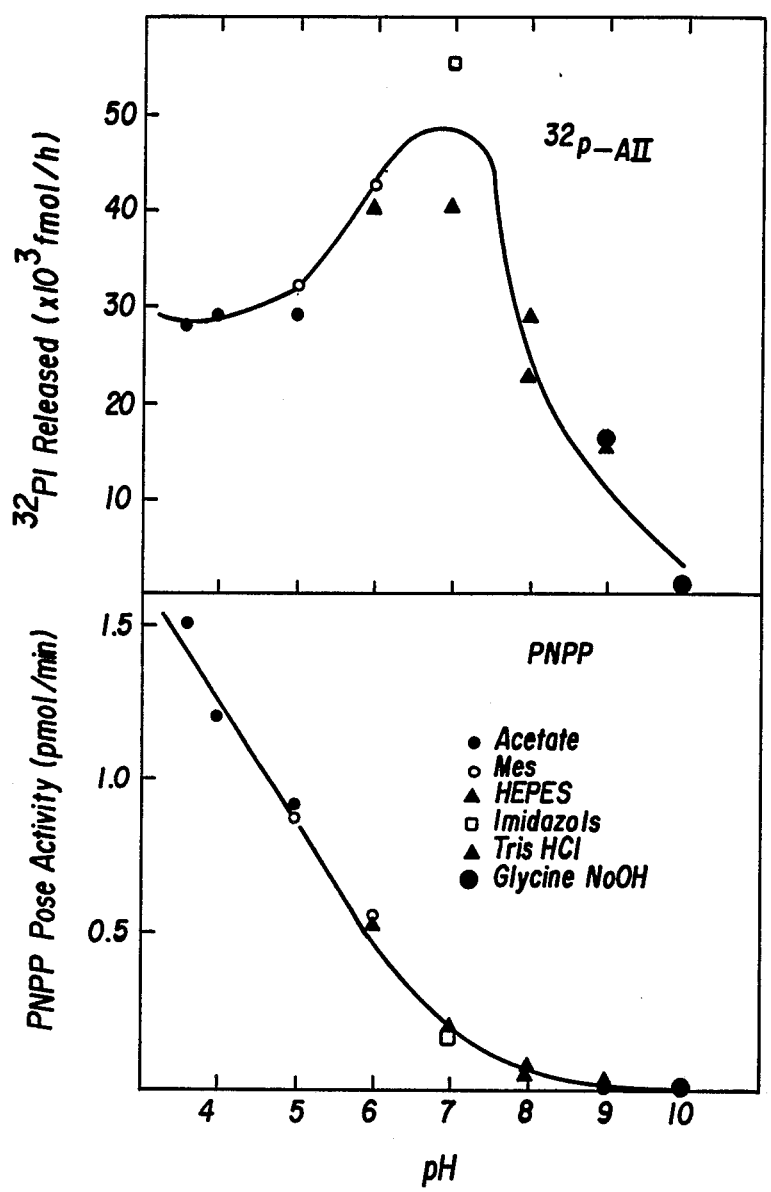

FIG. 7. pH Profile of the Purified Phosphatase Using $^{32}$P-Tyr Angiotensin II and PNPP as substrates. Assay conditions were as described in the Example.

Figure 8:
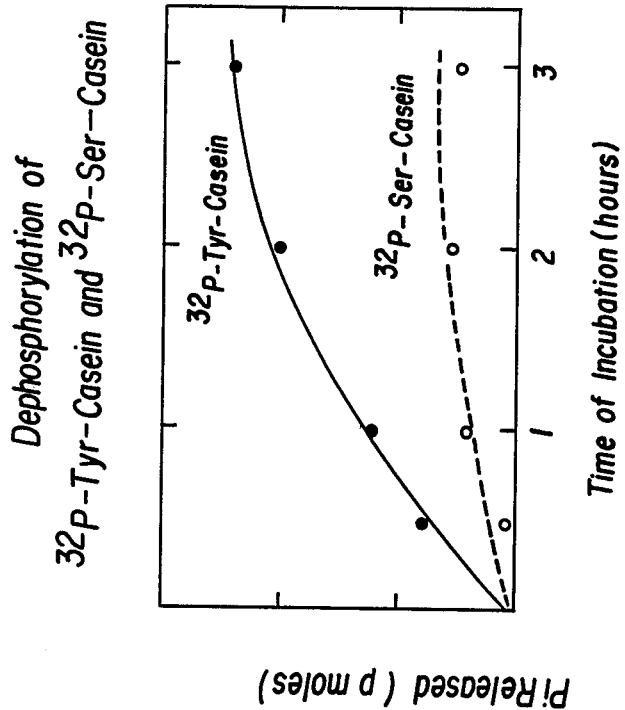

FIG. 8. Dephosphorylation of $^{32}$P-Tyr-casein and $^{32}$P-Ser-casein. $^{32}$P-Tyr-casein and $^{32}$P-Ser-casein were prepared as described under Materials and Methods. 0.01 μM Pi of each substrate was incubated at 30° with the purified enzyme in a buffer containing 4 mM imidazole, pH 7.2, 10% glycerol, 0.1M NaCl, 0.2% Triton X-100. At the end of the incubation, phosphoproteins were precipitated by 10% TCA with BSA added as carrier. The radioactivity remaining was determined by filtration on Whatman GF/F filters after washing with 4×2.5 ml of 10% TCA with 10 mM sodium pyrophosphate. Pi released was calculated by difference of remaining from added radioactivity. Control incubation of either substrate with buffer alone showed no decrease in precipitable radioactivity with time.

Figure 9:
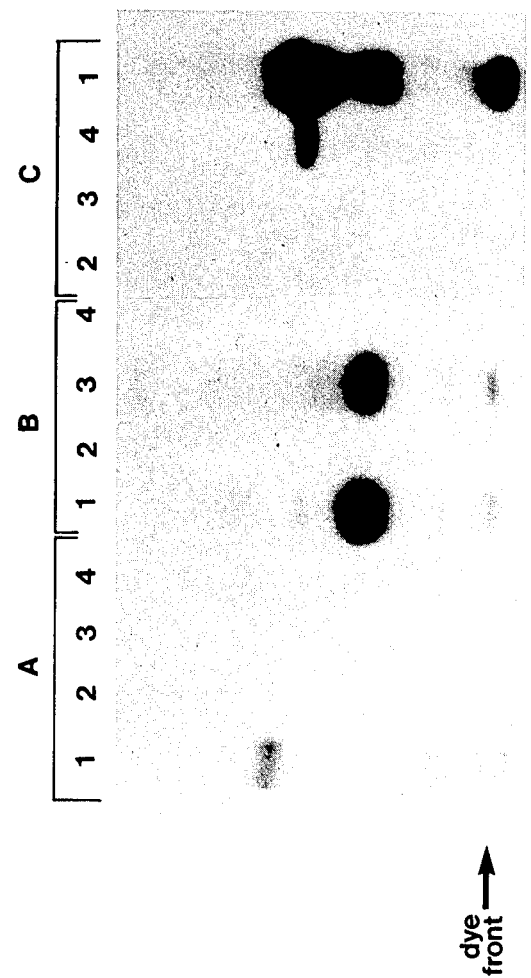

FIG. 9. Immunological Characterization of the Purified Phosphotyrosyl Protein Phosphatase. 3–5 μg of the purified enzyme, commercially available human placental alkaline phosphatase and human prostatic acid phosphatase were iodinated as described in the Example. Approximately 10,000 cpm of each of the iodinated protein was reacted with (1) buffer alone, (2) normal rabbit serum, (3) rabbit anti-human prostatic acid phosphatase, and (4) rabbit anti-human alkaline phosphatase. After an overnight incubation at 4° C., 50 ml of a 1:1 mixture of Protein A Sepharose was added and incubated for one hour at room temperature. Non-specifically bound protein was washed off by sequential washes as described in the Example. Specifically bound proteins were extracted by the SDS gel electrophoresis sample buffer with 10% mercaptoethanol, and electrophoresis was done on 8.5% polyacrylamide gels. After drying the gels, iodinated proteins were visualized by autoradiography: A. Phosphotyrosyl protein phosphatase purified from human placental membranes. B. Human prostatic acid phosphatase. C. Human placental alkaline phosphatase.

The following example is provided in order that the instant invention might be more fully understood. It should not be construed as being limitative of this invention.

EXAMPLE

Preparation and Solubilization of Human Placental Membranes

Human placenta was obtained from a nearby hospital within 1 hour after delivery and was chilled on ice. The supporting membranes were removed and the tissue was washed with 10 mM Tris, pH 7.4, 0.15M NaCl and homogenized in a buffer containing 0.25M sucrose, 25 mM benzamidine, 5 mM EDTA and 0.2 mM PMSF in a Waring blender. The homogenate was centrifuged at 10,000×g for 30 minutes in a Beckman centrifuge. The supernatant was centrifuged at 100,000×g for one hour in two Ti 45 rotors in Beckman ultracentrifuges. The membrane pellets were resuspended and washed with 40 mM imidazole, pH 7.2, and 0.2M NaCl and repelleted by centrifugation at 100,000×g for one hour. The final membrane preparation was resuspended at approximately 20–50 mg/ml of protein in the above buffer.

The washed membranes were solubilized with 2% Triton X-100 at a protein concentration of 5 mg/ml at 4° for 30 minutes. The unsolubilized residues were removed by centrifugation at 140,000×g for 30 minutes.

Purification of a Phosphotyrosyl Protein Phosphatase

All of the following procedures were carried out at 4° C. except where noted. Wheat Germ Lectin Affinity Column Chromatography Wheat germ lectin agarose was prepared by coupling 200 mg of wheat germ lectin to approximately 40 ml of cyanogen bromide activated Sepharose 4B from Pharmacia according to the manufacturer's instructions. Approximately 400 mg of solubilized membrane protein was loaded on such a lectin affinity column equilibrated with a buffer containing 40 mM imidazole, pH 7.2, 10% glycerol, 0.2% Triton X-100 and 0.5M NaCl collecting 5 ml fractions. The column was washed extensively with the same buffer and eluted with 0.3M N-acetyl glucosamine in the same buffer. Aliquots of each fraction were taken for determination of protein concentration by the method of Bradford. Phosphatase activity using both PNPP and $^{32}$P-Tyr angiotensin II as substrates were also determined.

Preparative DEAE-HPLC

The fractions eluted by N-acetylglucosamine from two similar lectin columns were pooled and dialyzed against 40 mM imidazole, pH 7.2, 10% glycerol, 0.2% Triton X-100 (IGT buffer) overnight at 4° C. and loaded onto a DEAE 5SW HPLC column (Bio Rad Laboratories) equilibrated with the same buffer. Elution was done on a 500 ml 0–0.4M NaCl gradient in IGT buffer using a flow rate of 1.5 ml/minute.

Hydroxyapatite Column Chromatography

Pooled fractions from the DEAE column were loaded onto 20 ml of BioGel HT (Bio Rad Laboratories) equilibrated in IGT buffer. Elution was done initially with a 200 ml 0–50 mM potassium phosphate gradient, pH 7, in 10% glycerol and 0.2% Triton X-100. Subsequent elution was done with a 100 ml gradient of 50–400 mM potassium phosphate, pH 7, in 10% glycerol and 0.2% Triton X-100 to remove absorbed proteins.

Second DEAE-HPLC

A second DEAE-HPLC step was performed after dialysis of the pooled fractions against IGT buffer. Similar conditions as in the first DEAE-HPLC column were employed except that a 500 ml gradient of 0–300 mM NaCl in IGT buffer was used.

Iodination and Immunological Characterization

3–5 mg protein of purified human prostatic acid phosphatase, human placental alkaline phosphatase, and the purified phosphatase were iodinated each with 250 mCi of Na-$^{125}$I in the presence of chloramine T (0–25 mg/ml) in 50 mM Tris, pH 6.5, for 30 seconds at room temperature. Free iodide was removed by desalting the samples on Sephadex G50 columns. Immunoprecipitation was carried out at 4° C. overnight using approximately 10,000 cpm of iodinated proteins in 25 ml and 10 ml of undiluted normal rabbit serum, rabbit anti-human prostatic acid phosphatase, or rabbit anti-human alkaline phosphatase antisera. 50 ml of a 1:1 suspension of protein A-Sepharose was added to each incubation to precipitate the immunoglobulins. After sequential washings of the Protein A Sepharose beads with 10 mM Tris HCl, pH 7.5, 0.5% w/v NP-40 (NT buffer), NT buffer with 1 mM EDTA, NT buffer with 0.5M NaCl, and NT buffer with 0.1% w/v SDS, the specifically bound proteins were eluted in the SDS gel electrophoresis sample buffer with 10% mercaptoethanol and subjected to gel electrophoresis on 8.5% polyacrylamide gels. Autoradiography of the dried gels was done using Kodak XAR-5 film with intensifying screens.

Other Experimental Procedures

Gel electrophoresis in the presence of sodium dodecyl sulfate was performed as described by Laemmli (Nature (London) 227 pp. 680–685 (1970)) and stained with silver nitrate (Bio Rad Laboratories). Protein concentrations were determined by Coomassie G250 dye binding using gamma globulin as standard (Bio Rad Laboratories).

Purification of Human Phosphotyrosyl Protein Phosphatase

Human placental membrane fraction was solubilized with Triton X-100 and subjected to wheat germ lectin agarose affinity chromatography. The proteins retained by the lectin gel were eluted with N-acetylglucosamine. Phosphatase activities were assayed using p-nitrophenyl phosphate and $^{32}$P-angiotensin II as substrates in acetate buffer, pH 5, giving the chromatographic profiles shown in FIG. 2. The N-acetylglucosamine eluted peak contained 20% of protein originally loaded on the column, 70% of the p-nitrophenyl phosphatase activity and 26% of the $^{32}$P-Tyr-angiotensin II phosphatase activity. The specific activity of p-nitrophenyl phosphatase was 10 fold higher for the eluted fractions than for the unretained fractions, while the specific activity of the $^{32}$P-Tyr-angiotensin phosphatase was only 1.4 fold higher in the eluted fractions than in the unretained fractions. However, under these chromatographic conditions, 95% of the epidermal growth factor receptor kinase activity was retained and eluted from the column by N-acetylglucosamine, indicating that the column was not overloaded. Our present studies focus on the glycoprotein phosphatases retained by this lectin column.

The phosphatase peak fractions eluted from the lectin column were pooled and dialyzed to lower salt concentrations. This preparation was loaded onto a DEAE-HPLC column and the retained proteins were eluted with a linear NaCl gradient. FIG. 3 shows the elution profiles. When $^{32}$P-Tyr-angiotensin II phosphatase activity was assayed at pH 5 in the absence of divalent cations, two peaks of activity were found. A sharp peak was eluted at 0.1 M NaCl and was found to correspond to the major peak of alkaline PNPP phosphatase activity assayed at pH 10 in the presence of 10 mM MgCl$_2$. A second peak was eluted at 0.15M NaCl and corresponded to the acid PNPP phosphatase activity assayed at pH 5 in the absence of divalent cations. Since alkaline phosphatase has been well characterized, we focused our attention on the second peak.

Only the peak fractions of acid phosphatase were pooled since the shoulder fractions could represent different enzymes. The pooled sample was loaded onto a hydroxyapatite column and the column was initially eluted with a shallow phosphate gradient (0–50 mM) followed by a steep gradient (50–400 mM). A minor peak of acidic PNPPase activity was unretained, while the major PNPP phosphatase activity was eluted around 5 mM phosphate (FIG. 4). The $^{32}$P-Tyr-angiotensin II phosphatase activity showed a similar profile. However, the phosphate carried over from the samples interfered with the extraction of free-$^{32}$P from the reaction solution and could not be accurately corrected, interfering with the quantitation of the angiotensin II assay in the higher salt sample. Several representative fractions, among fraction numbers 30–80, with higher phosphate concentrations were dialyzed before assaying and showed no PNPP phosphatase or $^{32}$P-Tyr-angiotensin phosphatase activity.

The peak of phosphatase activity was further purified by a second chromatography on preparative DEAE-HPLC. The PNPP phosphatase activity was eluted at 0.15M NaCl as in the first DEAE-HPLC column (FIG. 5). When aliquots of the peak fractions were subjected to SDS polyacrylamide gel electrophoresis and then the gel stained with silver nitrate, the intensity of staining of a band corresponding to a Mr of 73,000 corresponded to the peak of activity. FIG. 6 shows that this Mr 73,000 band migrated differently from either human placental alkaline phosphatase or human prostatic acid phosphatase (available commercially) under reducing conditions. When electrophoresis was done under non-reducing conditions, the same Mr 73,000 band was seen. However, when a sample of the pure enzyme was subjected to gel filtration on a TSK HPLC column in the presence of 0.2% Triton X-100, the activity eluted in a single symmetrical peak corresponding to an estimated MW of 200,000. It is not clear whether this reflects the non-globular nature of the protein or whether the enzyme consists of several noncovalently linked subunits. The purity of the enzyme was also confirmed when the preparation was iodinated and subjected to SDS gel electrophoresis. Autoradiography of the dried gel showed a major band corresponding to the Mr 73,000 band (FIG. 9). A minor band with low molecular weight corresponded to a faint band on the silver stained gel, the intensity of which did not correspond to the peak of phosphatase activity.

pH Optima of the Phosphotyrosyl Protein Phosphatase

FIG. 7 shows the pH profiles of the highly purified phosphatase using $^{32}$P-Tyr-angiotensin II and PNPP as substrates. The PNPP phosphatase activity decreased as the pH increased from 3.5 to 10. The PNPP phosphatase activity was assayed at pH 4 and 6 at various concentrations of PNPP and the Km values were determined by Lineweaver-Burk plots to be 0.77 mM at pH 4 and 0.42 mM at pH 6. The $K_{cat}$ values were 1.02 μmol/min/mg protein and 0.39 μmol/min/mg protein at pH 4 and pH 6, respectively. In contrast, when $^{32}$P-Tyr-angiotensin II was used as substrate, the pH optimum was 7. Different pH optima for PNPP and $^{32}$P-histone have also been observed with purified alkaline phosphatase from calf intestine and E. coli. The neutral pH optimum of this placental phosphatase for a phosphorylated peptide suggests that this enzyme may play a role in the dephosphorylation of phosphotyrosyl proteins in cells.

Substrate Specificity of the Enzyme

The purified enzyme catalyzed the dephosphorylation of $^{32}$P-Tyr-casein (0.25 nmoles/hour/mg and 0.07 nmoles/hour/mg) (0.01 μM Pi) at initial rates that were 3.5 times higher than that for $^{32}$P-Ser-casein (FIG. 8). Similarly, when $^{32}$P-Tyr-histone f2b and $^{32}$P-Ser-histone f2b were used at substrates (0.01 μM Pi), the rate of dephosphorylation of the P-Tyr substrate was 3.3X that for the P-Ser substrate (0.05 nmoles/hour/mg and 0.015 nmoles/hour/mg, respectively). Thus, the purified phosphatase dephosphorylated $^{32}$P-Tyrcasein at rates 10 fold higher than that for $^{32}$P-Tyr-histone f2b. It has been reported that phosphorylated basic proteins, such as histones and peptides such as angiotensin II, were poor substrates for the phosphotyrosyl protein phosphatases purified from rabbit kidney cytosol (19). It appears that this substrate specificity also holds for this enzyme.

Effect of Phosphatase Inhibitors

Table 1 shows the effects of various alkaline or acid phosphatase inhibitors on the PNPP phosphatase activities of the purified enzyme and on the pure alkaline phosphatase of human placental membranes and the acid phosphatase of human prostate. The enzyme described in this report was nearly completely inhibited by 10 μM molybdate, 5 mM L-tartrate, 5 mM NaF and 100 μM vanadate. It is slightly inhibited by phosphotyrosine and rather insensitive to ZnCl. These properties are similar to those of the prostatic acid phosphatase. However, this enzyme was stimulated by EDTA (79%) and phosphoserine (73%), whereas the prostatic enzyme was not affected by EDTA and was slightly inhibited by phosphoserine. When $^{32}$P-Tyr-angiotensin II was used as substrate, the purified enzyme was similarly inhibited by 10 μM molybdate, 5 mM tartrate, 5 mM NaF, 10 μM vanadate and 10 mM phosphotyrosine (20.8, 27.6, 28.7, 46.4, and 11.5%, respectively). Similarly, 20 mM EDTA and 10 mM phosphoserine stimulated the enzymatic activity by 29.8% and 4.3%, respectively. 100 μM ZnCl$_2$, which was only slightly inhibitory on the PNPP phosphatase activity, inhibited $^{32}$P-Tyr-angiotensin II activity by only 4.2%. These results suggest that the phosphatase that we have purified is a unique enzyme, with biochemical properties different from those of previously described phosphatases.

Immunolooical Characterization

Commercially available antiserum against human alkaline phosphatase and human prostatic acid phosphatase were reacted with an iodinated preparation of the purified enzyme. FIG. 9 shows that while the respective antisera reacted with the phosphatases to which the sera were made, there was no cross reactivity of either of the antisera with the purified enzyme.

PREPARATIONS p-Nitrophenyl phosphate (PNPP), wheat germ lectin, the catalytic subunit of cAMP-dependent protein kinase, histone f2b (Sigma type VII), casein, human semen acid phosphatase, and Protein A-Sepharose were purchased from Sigma. Angiotensin II was purchased from Boerhinger Mannheim. [65 -$^{32}$P]ATP (3000 Ci/mmol), I$^{125}$-sodium iodide and Aquasol II were purchased from New England Nuclear. Human placental alkaline phosphatase was purchased from Worthington Biochem. Epidermal growth factor (electrophoretically pure) was purchased from Biochemical Technologies Inc. (Cambridge, Mass). Rabbit anti-human placental alkaline phosphatase antiserum was purchased from Arnel Products, Inc. (New York, N.Y.). Rabbit anti-human prostatic acid phosphatase antiserum was purchased from Miles Scientific (Naperville, Ill.).

Preparation of $^{32}$P-Tyr-angiotensin II

Angiotensin II was phosphorylated by EGF receptor kinase from human placental membranes. Human placental membranes (2.5 mg/ml) were preincubated with EGF (0.3 μM dissolved in 1 mg/ml BSA) in a final volume of 2 ml containing 50 mM HEPES, pH 7, 0.1M NaCl, and 1 mM sodium vanadate for 15 minutes at 4° C. After addition of angiotensin II to a final concentration of 1 mM, the kinase reaction was started by the addition of a reaction mixture such that the final reaction contained 12 mM MgCl$_2$, 2 mM MnCl$_2$, 50 mM PNPP, 100 μM ATP and 800 μCi [γ-$^{32}$P]-ATP. The reaction was incubated at 4° C. for 30 minutes and terminated by centrifugation at 100,000×g for 30 minutes to remove membranes. The supernatant was mixed with an equal volume of 0.2% trifluoroacetic acid in water and loaded on a hydrated Sep Pak (Waters Associates). The free [γ-$^{32}$P]-ATP was removed by washing the Sep Pak with 10×10 ml of 0.2% TFA in water. The phosphorylated angiotensin II was eluted with 80% acetonitrile and 0.2% trifluoroacetic acid in water. The fractions containing radioactivity were pooled and evaporated to dryness under nitrogen. The phosphorylated angiotensin II was taken up in 0.25 ml of water containing 1 mg/ml BSA.

Preparation and Phosphoamino Acid Analysis of Phosphorylated Protein Substrates Histone f2b and casein were phosphorylated on serine/threonine residues in a final volume of 1 ml containing 50 mM Tris, pH 7.5, 25 mM MgCl$_2$, 1 mM dithiothreotol, 5 mg/ml histone f2b or 10 mg/ml casein, 50 μM ATP, 250 μCi [γ-$^{32}$P]-ATP and approximately 60 units of the catalytic subunit of cAMP-dependent protein kinase. The reaction was carried out overnight at room temperature with rotation and terminated by precipitation with 25% TFA. The pellets were taken up in 1 ml of 20 mM HEPES, pH 7, and dialyzed extensively against the same buffer.

Histone f2b and casein were phosphorylated on tyrosine residues using insulin-stimulated insulin receptor kinase from the N-acetyl-glucosamine eluted peak from the lectin agarose affinity column loaded with solubilized human placental membranes. Approximately 80 µg of protein from the lectin column was preincubated with 1 µM insulin in a final volume of 500 µl containing 20 mM HEPES, pH 7.4, 30 mM NaCl, 1 mM $MnCl_2$, 100 mM sodium vanadate, 12 mM PNPP at room temperature for 15 minutes. The kinase activity was started by the addition of a reaction mixture such that the final concentration of ATP was 50 µM with 125 µCi of [γ-$^{32}$P]-ATP. Histone f2b was added to a final concentration of 1 mg/ml and casein was added to a final concentration of 3 mg/ml. The reaction was carried out at room temperature for 15 minutes and terminated by precipitation with 10% TCA. The precipitated proteins were treated with 0.5N NaOH at 55° C. for 60 minutes to hydrolyze any phosphorylation on Ser/Thr residues. The solution was neutralized with 0.5M HCl and reprecipitated with 10% TCA. The pellet was taken up in 100 µl of 20 mM HEPES, pH 7, and dialyzed extensively against the same buffer.

The phosphorylated proteins were partially hydrolyzed with 6N HCl at 100° under vacuum for 2 hours. The phosphoamino acids were analyzed on a Synchropak Q300 HPLC column (SynChrom, Inc., Linden, Ind.) by elution with 40 mM potassium phosphate, pH 4. FIG. 1 shows that the $^{32}$P-Ser/Thr-casein was mainly phosphorylated on serine residues and that the $^{32}$P-Tyr-casein was mainly phosphorylated on tyrosine residues. Similar results were obtained with phosphorylations using histone f2b.

Assays for Phosphotyrosine Phosphatase Activity

Phosphotyrosine phosphatase activity was measured by the release of $^{32}$Pi from $^{32}$P-Tyr-angiotensin II in a 100 ml reaction mixture containing 0.1M acetate, pH 5, 5 mM DTT, 2.5 mg/ml BSA and 0.05 mM $^{32}$Pi of $^{32}$P-Tyr-angiotensin II. After incubation at 30° for 30 minutes, the reaction was terminated by the addition of 100 ml of 10% TCA. 0.2 ml of 1.25 mM $KH_2PO_4$ in 1N $H_2SO_4$ was added as carrier. 0.1 ml of 5% ammonium molybdate was then added. After extraction with 0.5 ml of 1:1 isobutanol:benzene, 0.25 ml of the upper phase was taken and mixed with 10 ml Aquasol II to be counted in a packard scintillation counter.

p-Nitrophenylphosphatase activity was determined in a final volume of 500 ml containing 100 mM acetate, pH 5, 5 mM DTT, 2.5 mg/ml BSA and 1 mM PNPP. The reaction was carried out at 30° C. and terminated with 0.5 ml of 0.2N NaOH. Alkaline PNPP phosphatase activity was similarly determined except that 50 mM glycine NaOH, pH 10, was used as buffer and 10 mM $MgCl_2$ was included in the reaction mixture. Absorption at 410 nm wavelength was recorded on a Gilson spectrophotometer. Units of phosphatase activity were calculated with a millimolar extinction coefficient of 17.5 for p-nitrophenol at 410 nm and pH 11.

Phosphatase activity against phosphorylated proteins was measured by incubation of the substrates at 0.01 mM Pi with the purified enzyme at pH 7. At the end of the incubation at 30° C. the protein substrates were precipitated by 10% TCA with added BSA as carrier and the radioactivity remaining was determined by filtration on Whatman GF/F filters after washing with 4×2.5 ml of 10% TCA with 10 mM sodium pyrophosphate. Control incubations of the substrates with buffer alone showed no decrease in precipitable radioactivity with time.

What is claimed is:

1. A human phosphotyrosyl protein phosphatase enzyme characterized in having a molecular weight of approximately 200,000 as determined by gel filtration high pressure liquid chromatography; a subunit molecular weight of approximately 73,000 as shown by SDS reducing gel electrophoresis; being a dephosphorylating enzyme with characterizing percentage inhibition of dephosphorylation in the present of phosphatase inhibitors as follows:

| | |
|---|---|
| 10 µM molybdate | −96.4% |
| 5 mM L-tartrate | −98.1% |
| 5 mM NaF | −96.7% |
| 20 mM EDTA | +78.9 |
| 100 µM $ZnCl_2$ | −14.9 |
| 10 µM Vanadate | −38.2 |
| 10 mM p-tyrosine | −21.6 |
| 10 mM p-serine | +73.4 | an SDS gel electrophoresis substantially as shown in FIG. 6; a pH profile using $^{32}$P-Tyr angiotensin II and PNPP as substrates substantially as shown in FIG. 7; a rate of dephosphorylation of $^{32}$P-Tyr-casein and $^{32}$P-Ser-casein substantially as shown in FIG. 8; and an immunological profile substantially as shown in FIG. 9.

2. The human phosphotyrosyl protein phosphatase enzyme of claim 1 which is isolated from human tissues high in insulin receptors.

3. The human phosphotyrosyl protein phosphatase enzyme of claim 2 which is isolated from placental membranes, liver, adipose, brain or muscle.

4. The human phosphotyrosyl protein phosphatase enzyme of claim 3 which is isolated from placental membranes.

* * * * *